US009687329B2

(12) United States Patent
Lee (10) Patent No.: US 9,687,329 B2
(45) Date of Patent: Jun. 27, 2017

(54) ELECTRIC TOOTHBRUSH

(71) Applicant: Wang Ken Lee, Marietta, GA (US)

(72) Inventor: Wang Ken Lee, Marietta, GA (US)

( * ) Notice: Subject to any disclaimer, the term of this patent is extended or adjusted under 35 U.S.C. 154(b) by 273 days.

(21) Appl. No.: 14/468,463

(22) Filed: Aug. 26, 2014

(65) Prior Publication Data

US 2015/0052695 A1    Feb. 26, 2015

Related U.S. Application Data

(60) Provisional application No. 61/869,808, filed on Aug. 26, 2013.

(51) Int. Cl.
*A61C 17/22* (2006.01)
*A46B 15/00* (2006.01)
*A61C 17/34* (2006.01)
*A61C 17/26* (2006.01)

(52) U.S. Cl.
CPC ........ *A61C 17/221* (2013.01); *A46B 15/0004* (2013.01); *A46B 15/0008* (2013.01); *A46B 15/0044* (2013.01); *A61C 17/22* (2013.01); *A61C 17/225* (2013.01); *A61C 17/26* (2013.01); *A61C 17/349* (2013.01); *A61C 17/3436* (2013.01); *A46B 2200/1066* (2013.01)

(58) Field of Classification Search
CPC ....... A46B 13/02; A61C 17/22; A61C 17/221; A61C 17/225; A61C 17/24; A61C 17/26; A61C 17/32; A61C 17/34; A61C 17/3409; A61C 17/3436; A61C 17/349
USPC ................................ 15/4, 22.1, 22.2, 23, 28
See application file for complete search history.

(56) References Cited

U.S. PATENT DOCUMENTS

| | | | | |
|---|---|---|---|---|
| 5,493,747 A * | 2/1996 | Inakagata | .......... | A61C 17/3418 15/22.1 |
| 5,561,881 A * | 10/1996 | Klinger | .............. | A46B 15/0002 15/105 |
| 5,784,742 A * | 7/1998 | Giuliani | ............. | A46B 15/0002 15/167.1 |
| 2002/0039720 A1* | 4/2002 | Marx | ...................... | A61C 17/26 433/216 |
| 2008/0189886 A1* | 8/2008 | Jimenez | ............... | A61C 17/349 15/22.4 |
| 2010/0141185 A1* | 6/2010 | Benning | .............. | A61C 17/221 318/139 |
| 2011/0289702 A1* | 12/2011 | Lee | ......................... | A61C 17/26 15/22.1 |
| 2012/0192367 A1* | 8/2012 | Lin | ...................... | A61C 17/224 15/22.1 |

* cited by examiner

*Primary Examiner* — Mark Spisich (57) ABSTRACT

An approach is provided a device for an electric toothbrush. The device comprises a brush head, a motor and a controller. The brush head has multiple exposed brush sets. The motor is connected to the brush head which is configured for driving the exposed brush sets. The controller drives the motor with a power module, and sensing a current of the motor which drives the motor in a pulse activated mode when the sensed current exceeds the predetermined current threshold. The pulse activated mode will make the bristle tuft rotary motion in a pulsating bristle tuft motions, and a person can be physically noticed through gums and teeth that reminds the person to release the brush pressure. The controller will disable the motor and warn the person if the brush pressure remains in a predetermined period of time.

5 Claims, 8 Drawing Sheets

ELECTRIC TOOTHBRUSH

RELATED APPLICATION

This application claims benefit of U.S. Provisional Application No. 61/869,808, filed Aug. 26, 2013.

FIELD OF THE INVENTION

Embodiments of the present invention relate to an electric toothbrush, particular to a device for an electric toothbrush that is able to stop brush operation and warn user when pressed forcibly against teeth and gums of the user.

BACKGROUND

A recent study shows that applying more pressure to teeth or brushing too long doesn't make them any cleaner and may increase the risk of oral health problems. Some electric toothbrush manufactures have also noticed this study, and therefore designed some electric toothbrushes with abilities of notifications when a person presses the brush at an excessive pressure unintentionally.

However, the known electric toothbrushes are mostly provided with a pressure sensor and a lighting indicator or speaker which inform the person to perform the tooth brushing at an optimum pressure level. Some reference documents such as U.S. Pat. No. 5,784,742A entitled "Toothbrush with adaptive load sensor", U.S. Pat. No. 7,120,960B2 entitled "Electric toothbrushes", and U.S. Pat. No. 5,493,747 entitled "Electric toothbrush".

The disadvantages of such electric toothbrushes are that a person may accidentally ignore the notifications. For example, for those toothbrushes with lighting indicator, a person requires to brush their teeth facing to a mirror in order to see the lighting indicator. Sound indicator can also be ignored if a person is in an noise environment.

Accordingly, it is desired to seek means or a mechanism to provide an electric toothbrush with better notifications when pressing the brush at an excessive pressure from a person. The person can be physically noticed through gums and teeth that reminds the person to release the brush pressure.

SOME EXEMPLARY EMBODIMENTS

These and other needs are addressed by the present invention, wherein an approach is provided for a device for electric toothbrush that is able to physically inform user when pressing pressure against teeth and gums has exceed a predetermined threshold.

According to an aspect of the present invention, an embodiment of the device provides a pulse activated mode to make the rotary motions of bristles in a pulsating bristle tuft motions, so that the person can be physically noticed through gums and teeth during brushing.

According to an embodiment of the present invention, a device for electric toothbrush comprises a brush head, a motor and a controller. The brush head has a plurality of exposed brush sets. The motor is connected to the brush head, which is configured for driving the exposed brush sets. The controller driving the motor with a power module, and sensing a current of the motor which disables the motor after a first predetermined period when the sensed current exceeds a predetermined current threshold.

The controller initially drives the motor in a Direct Current (DC) mode, and drives the motor in a pulse activated mode when the sensed current exceeds the predetermined current threshold.

According to another embodiment of the present invention, a device for toothbrush comprises a head portion housing, a middle portion housing and a handle portion housing. The head portion housing has a plurality of brush sets exposed from a front end of the head portion housing, and a torque assembly inside the head portion housing which is configured to engaged with the brush sets. The middle portion housing is connected to a rear end of the head portion housing. A motor and a controller are placed inside the middle portion housing. The motor is configured for driving the torque assembly. The controller drives the motor, senses a current of the motor, and drives the motor in a pulse activated mode when a sensed current exceeds the predetermined current threshold. The handle portion housing being connected to the middle portion housing, and having a power module connected to the controller, which provides electrical power to the controller.

Accordingly, the device for an electric toothbrush in accordance with embodiments of the present invention are able to physically inform users when pressing pressure against the teeth and gums has exceed a predetermined threshold.

BRIEF DESCRIPTION OF THE DRAWINGS

The invention is illustrated by way of example, and not by way of limitation, in the figures of the accompanying drawings in which like reference numerals refer to similar elements and in which.

DESCRIPTION OF THE PREFERRED EMBODIMENT

A device for an electric toothbrush is disclosed. In the following description, for the purposes of explanation, numerous specific details are set forth in order to provide a thorough understanding of the present invention. It is apparent, however, to one skilled in the art that the invention may be practiced without specific details or with an equivalent arrangement. In other instances, well-known structures and devices are shown in block diagram form in order to avoid unnecessarily obscuring the embodiments of the present invention.

Figure 1:
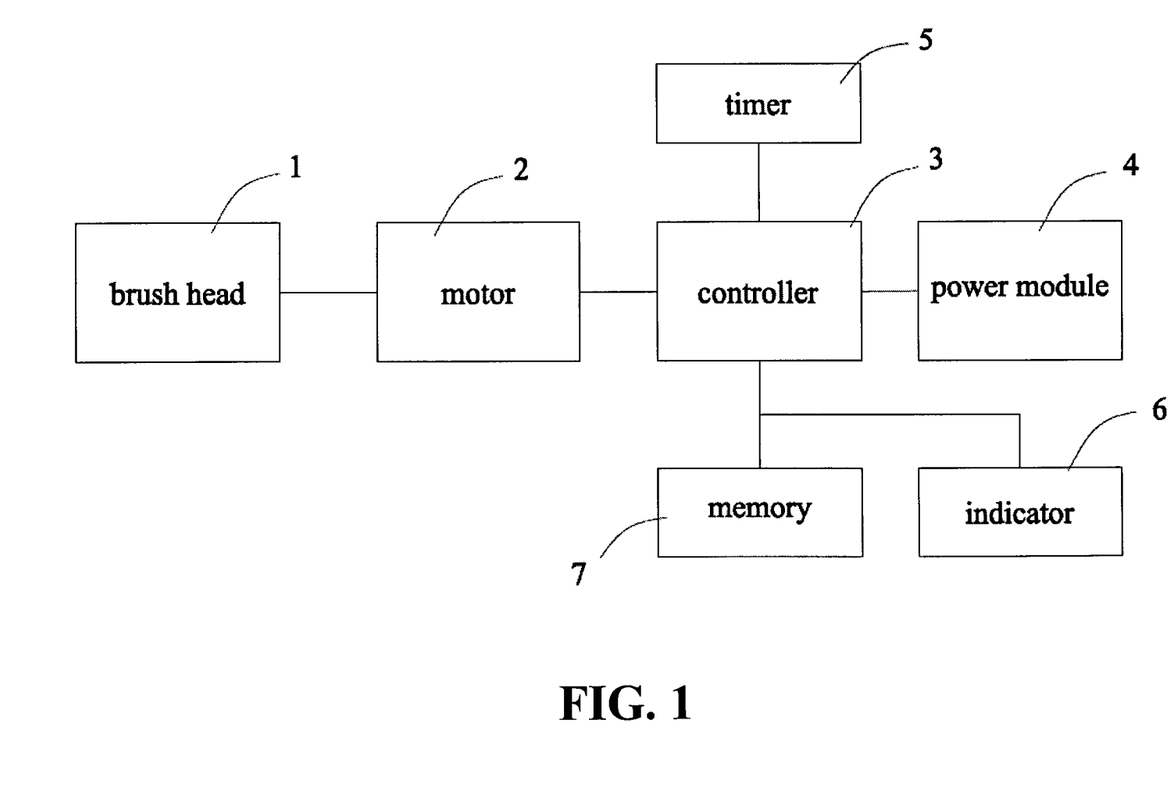
FIG. 1 is a block diagram illustrated a device for electric toothbrush in accordance with an embodiment of the present invention.

With reference to FIG. 1, FIG. 1 is a block diagram illustrated a device for electric toothbrush in accordance with an embodiment of the present invention. The device for an electric toothbrush comprises a brush head 1, a motor 2 and a controller 3. The brush head 1 has a plurality of exposed brush sets. The motor 2 is coupled to the brush head 1, and is configured for driving the exposed brush sets. The controller 3 is connected between the motor 2 and a power module 4, which is configured for driving the motor 2 with the power module 4, and senses the current of the motor 2 in order to control the operations of the motor 2. A person skilled in art will realized that the output torque of the motor is proportional to the amount of the current going into the motor, and the required torque is based on to the pressing pressure of the brush. Therefore, when the brush head is forcibly against teeth, the input current will increase as the torque of the motor increased.

Upon the pressing pressure against teeth and gums (i.e., the sensed current) exceeding a predetermined current threshold, the controller 3 will disable the motor 2 after a first predetermined period if the sensed current remains higher than the predetermined current threshold. In an embodiment, the first predetermined period may be 2~4 seconds. Once the sensed current exceeded the predetermined current threshold, the controller 3 will drive the motor 2 in a pulse activated mode. The duration of each pulse may be 150~700 micro-seconds and each gap between two pulses must greater than the duration of the pulse. Initially, the controller 3 drives the motor in a Direct Current (DC) mode (e.g., constant 4 volts (Vs) of the input voltage, and 1 ampere (A)) of the input current) when the sensed current by the controller 3 is below the predetermined current threshold (e.g., 2 A).

Further, in many studies shown that two minutes brushing time are the best brushing time for teeth cleaning, and thus, in an embodiment, the device may further comprises a timer 5 that counts an operational time of the motor 2, and instructs the controller 3 to disable the motor 2 when the operational time exceeds a second predetermined period. The second predetermined period is adjustable. On contrary, brushing time less than two minutes may also be considered as insufficient time for teeth cleaning, and therefore, by providing the timer 5 to count the operational time of the motor 2 is another good idea to tell user when is sufficient time for teeth brushing. For example, kids can be taught to brush their teeth until the device has automatically stopped.

Figure 2:
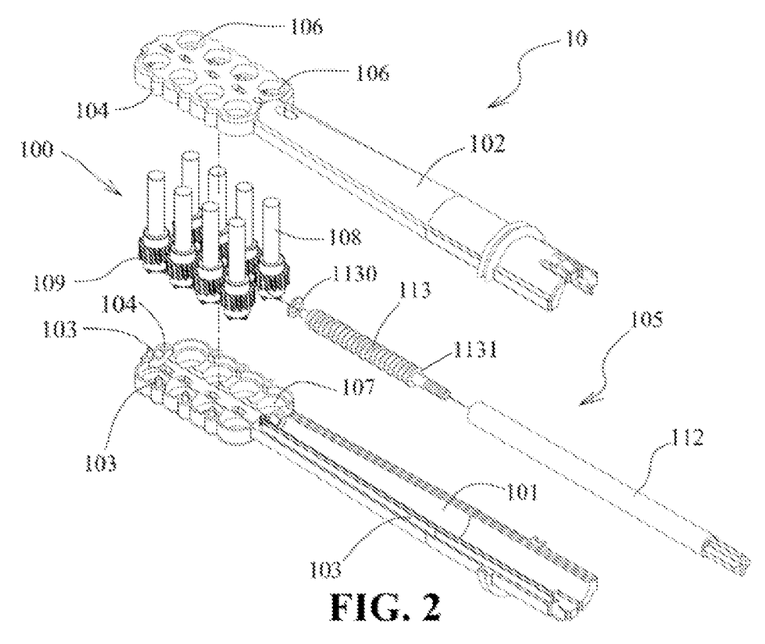
FIG. 2 is an exploded view diagram illustrating an exemplary embodiment of the head portion housing in accordance with the present invention.
Figure 3:
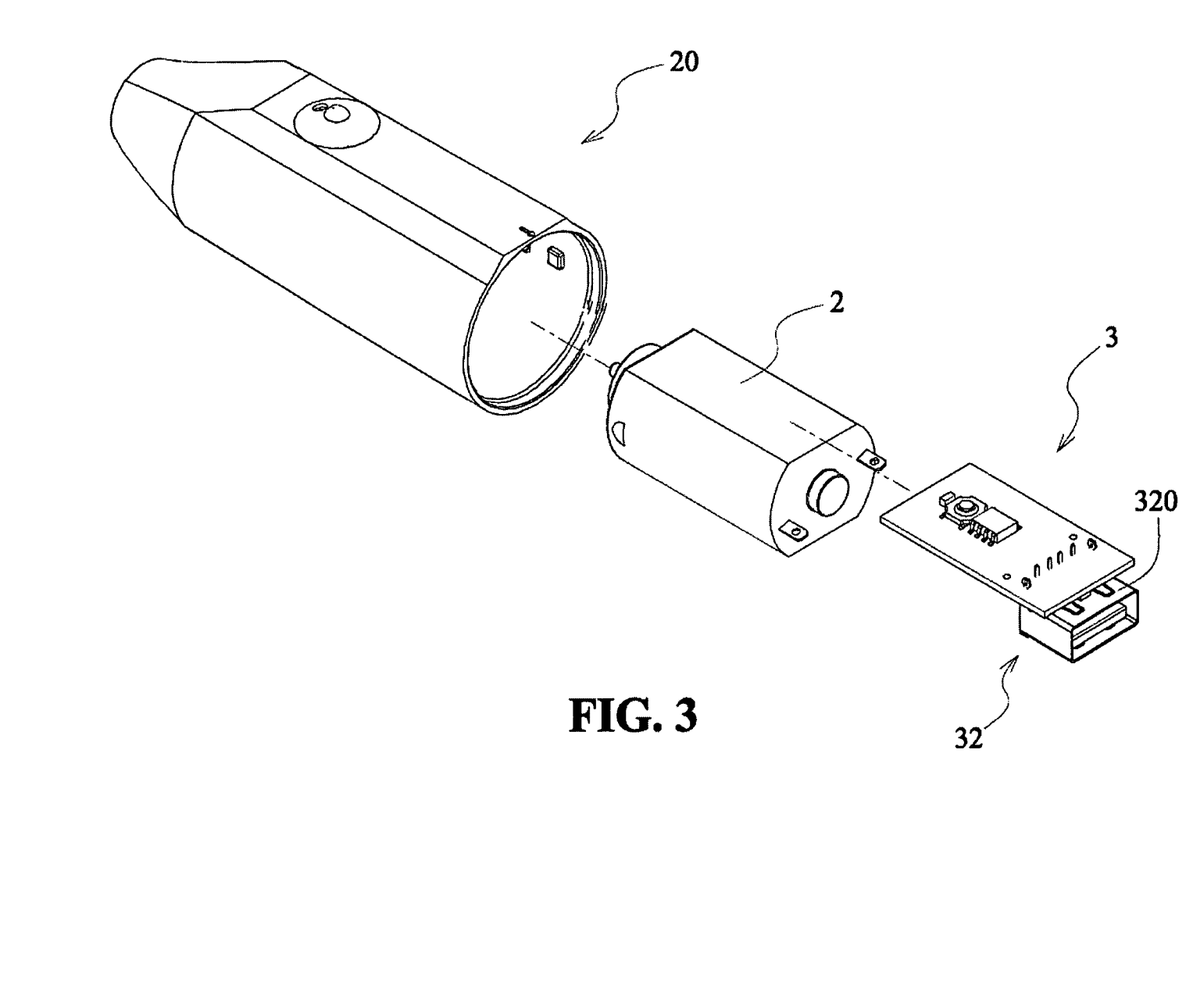
FIG. 3 is an exploded view diagram illustrating an exemplary embodiment of the middle portion housing in accordance with the present invention.
Figure 4:
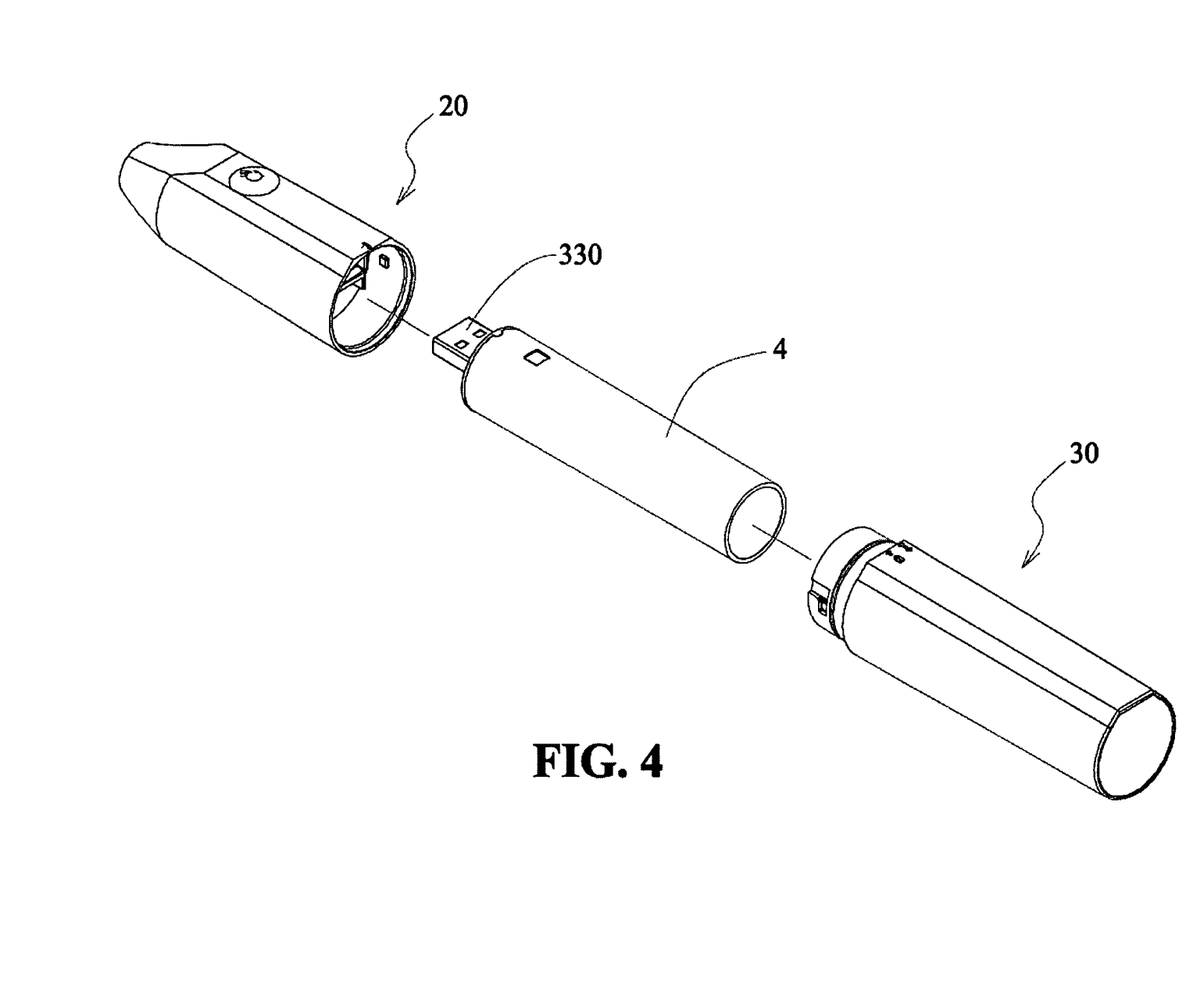
FIG. 4 is an exploded view diagram illustrating an exemplary embodiment of the handle portion housing in accordance with the present invention.

With further reference to FIGS. 2-4, FIG. 2 is an exploded view diagram illustrating an exemplary embodiment of the head portion housing in accordance with the present invention; FIG. 3 is an exploded view diagram illustrating an exemplary embodiment of the middle portion housing in accordance with the present invention; and FIG. 4 is an exploded view diagram illustrating an exemplary embodiment of the handle portion housing in accordance with the present invention.

In this embodiment, the device for an electric toothbrush comprises a head portion housing 10, a middle portion housing 20 and a handle portion housing 30. The head portion housing 10 is formed with a lower support base 101 and a upper cover 102. The lower support base 101 has multiple connecting protrusions 103 and multiple connecting concaves 104 distributively along the contour of a front end of the lower support base 101. The upper cover 102 has also multiple connecting protrusions 103 and multiple connecting concaves 104 corresponded to the corresponding connecting protrusions 103 and the connecting concaves 104 of the lower support base 101, and the depth of each connecting concave 104 is smaller than the length of each connecting protrusion 103. Since the connecting concave 104 is shorter than the length of the connecting protrusions 103, by applying an ultrasonic welding technique to the connecting protrusions is able to seal the upper cover 102 onto the lower support base 101.

The head portion housing 10 has a plurality of brush sets 100 exposed from a front end of the head portion housing 10, and a torque assembly 105 placed inside the head portion housing 10. As shown in FIG. 2, the upper cover 102 has multiple openings 106 at the front end of the head portion housing 10. The lower support base 101 has multiple recesses 107 corresponded to the openings 106 of the upper cover 102, which is configured to support the brush sets 100 as bristles 108 of the brush sets 100 exposed from the opening 106 of the upper cover 102. Each brush set 100 has a spiral gear 109 opposite to the opening 106 of the upper cover 102.

Figure 5:
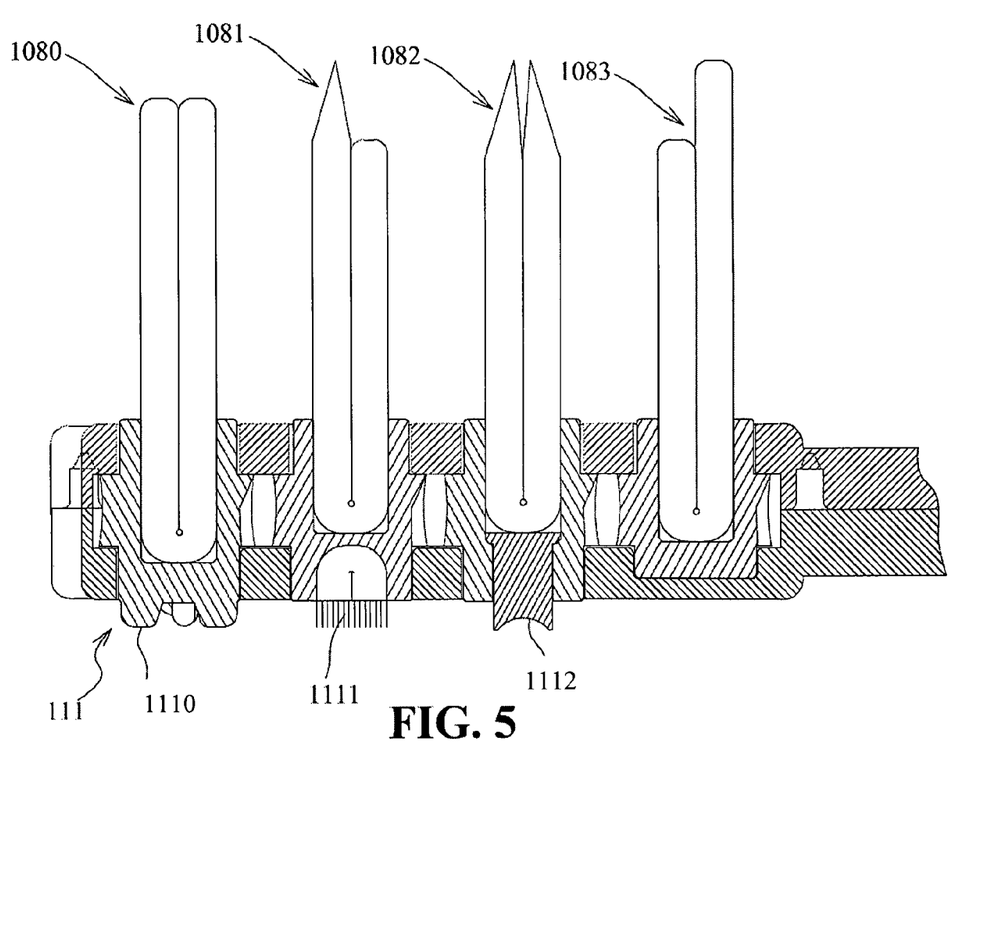
FIG. 5 is a partial side view of an embodiment of the bristles of the present invention.

With further reference to FIG. 5, illustrating a partial side view of another embodiment of the bristles. The brush sets 100 may have the same or mixed bristles 108, in this embodiment, the mixed bristles 108 are selected from a group consisting of a flat-tip bristles 1080, a tapered-tip bristles 1082, a hi-low flat-tip bristles 1083, a hi-low a tapered-tip bristles and a combination of single flat-tip and single tapered-tip bristles 1081. A person skilled in art will realize that the arrangement of types of bristle can be vary and mix-assembled to achieve individual preference.

In this embodiment, each recess 107 of the lower support base 101 has an optional hole 110 at a bottom of the recess, and each brush set 100 further comprises an optional secondary cleaning module 111 at a bottom thereof, which is penetrated through the holes 110 of the recesses 107. The secondary cleaning module 111 may be a tongue cleaning module 1110, a short bristle unit 1111 or a teeth polish head 1112.

As shown in FIGS. 2 and 3, the torque assembly 105 engages to the brush sets 100, and comprises a driving shaft 112 and a spiral shaft 113. The driving shaft 112 has a first end and a second end. The second end of the driving shaft 112 is coupled to the motor 2, and is rotated by the motor 2. The spiral shaft 113 is mounted on the lower support base 101. The spiral shaft 113 is connected to the first end of the driving shaft 112, and mesh with the spiral gear 109 on the other side. As the rotary motion of the motor 2 output drives the driving shaft 112 of the torque assembly 105, the spiral shaft 113 and the spiral gear 109 working in tandem. Therefore, the rotation of the driving shaft 112 drives the brush sets 100 to spin. The rotation of the driving shaft 112 can be in a direction of clockwise or anticlockwise based on the configuration of the controller 3 via the motor 2. In order to avoid damages to the lower support base 101 and the upper cover 102 during the rotations of the spiral shaft 113, the two ends of the spiral shaft 113 may further coupled with washer 1130 and/or shaped in a flat surface 1131.

As shown in FIGS. 2, 3 and 4, the motor 2 and the controller 3 are placed inside the middle portion housing 20, which the middle portion housing is connected to a rear end of the head portion housing 10. The handle portion housing 30 connects to the middle portion housing 20. The power module 4 is located inside the handle portion housing 30 and is connected to the controller 3, which is configured to energize the motor 2 with electrical power through the controller 3. In an embodiment of the present invention, the power module 4 may be a chargeable or non-chargeable battery pack. Since the power module 4 is connected to the controller 3, the device, as shown in FIG. 1, may further comprises an indicator 6 such as an LED light connected to the controller, and the indicator 6 is configured for indicating an user when the power volume of the power module 4 is below a volume threshold during use.

The controller 3 may further comprises a first USB module 32 with a female USB connector 320 inside the middle portion housing 20. The power module 4 further comprises a second USB module (not shown) with a male USB connector 330 extended outwardly from the handle portion housing 30. The USB modules (i.e., first and second USB modules) is an interface that transmit electrical power to the controller 3 and drive the motor 2.

Moreover, the controller, as shown in FIG. 1, may comprises a memory 7 unit that is able to record the operational statistics of the electric toothbrush such as the frequent use of the device. A person may also configure the controller from an external interface (e.g., a computer) via the first USB module, for example, a person may change the first or the second predetermined period. However, the controller 3 can be pre-programmed or customized programmed of thresholds, time period, brush set rotational revolution per minute and more.

Furthermore, the USB module can be considered as a wired transmitting module, and it can be replaced by other means of wired transmitting module. However, a person skilled in art realize that the wire transmitting module can further be replaced by an additional wireless module such as ZigBee® wireless module.

Figure 6A:
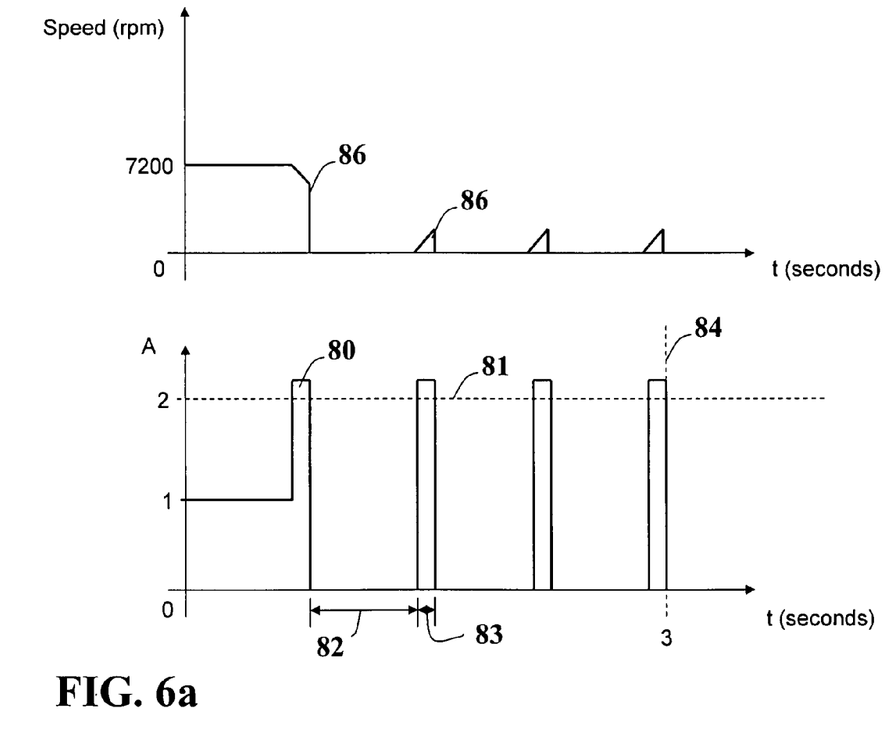
FIGS. 6a-6c are current waveforms of the motor to show how the controller controls the motor speed in response to the sensed current.
Figure 6B:
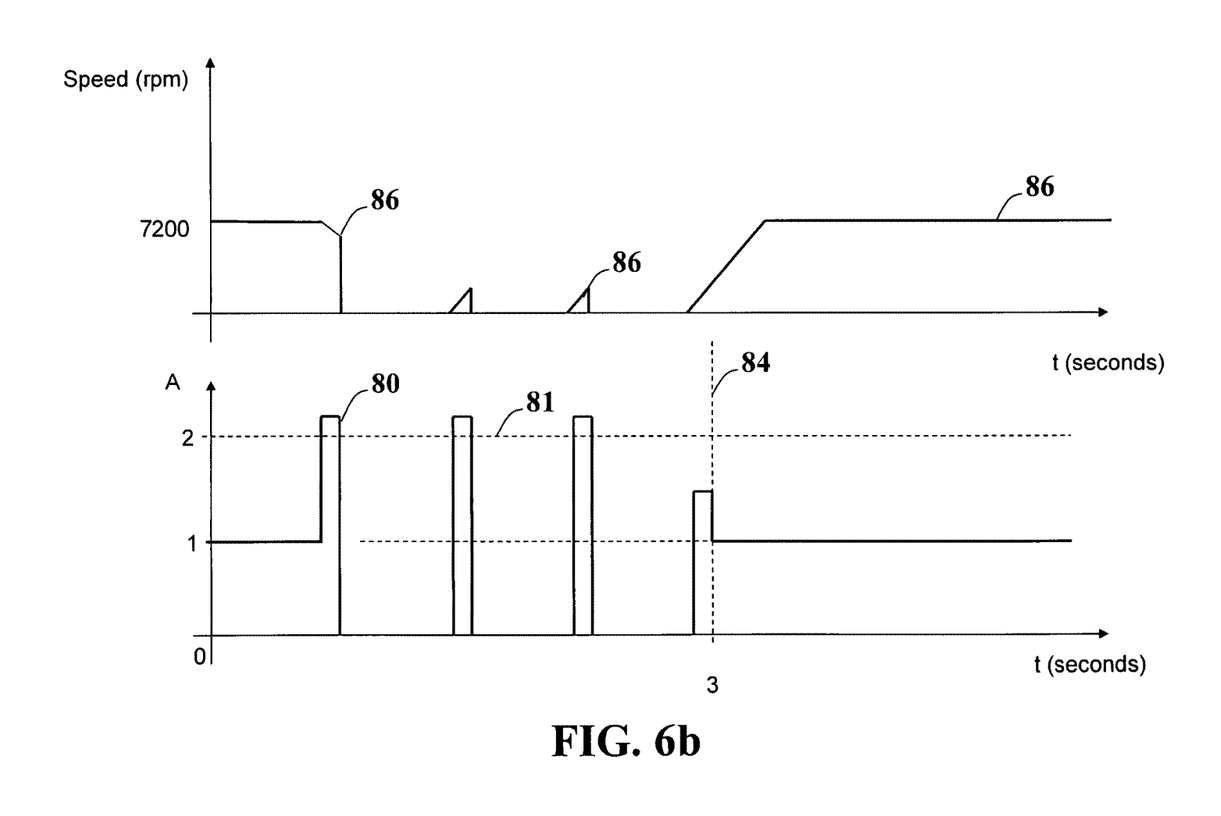
Figure 6C:
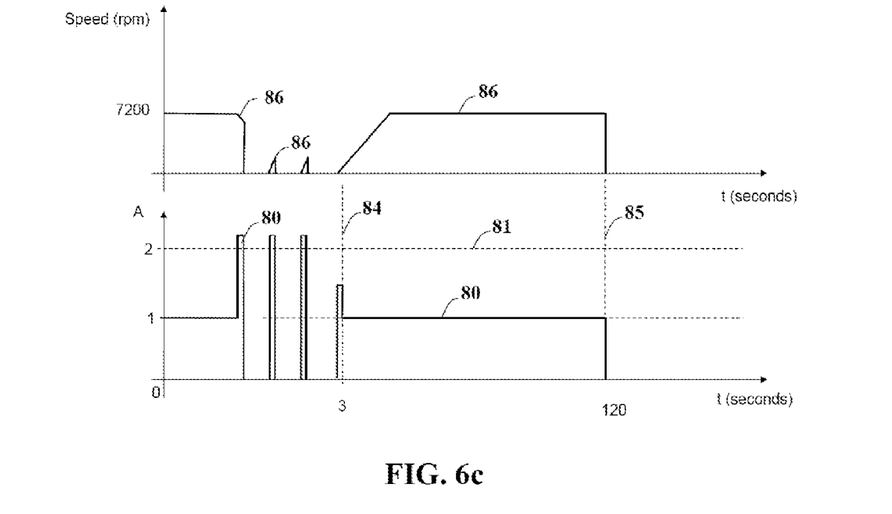

With reference to FIGS. 6a to 6c, illustrating current waveforms of the motor speed to show how the controller controls the motor in response to the sensed current. In this embodiment, the motor is energized from the DC mode (i.e., 1 ampere (A)) to the pulse activate mode, and the sensed current exceed the predetermined current threshold (i.e., 2 amperes). As shown in FIG. 6a, Once the sensed current 80 has reaches the predetermined current threshold 81, it means that a person might press the brush too hard against teeth and gums. The rotary speed 86 of the motor changes. The controller will disable the motor, so that the sensed current 80 and the rotary speed 86 of the motor will to zero. The controller then enable the motor again after a period of time (e.g., 0.5 to 1.2 seconds) and sensed again. If the following sensed current 80 is still higher or equal to the predetermined current threshold 81, the controller will disable the motor instantaneously or in a very short of time that forms a shape of a pulse. The duration 83 between the raising edge and the falling edge may be in a range of 150~700 micro-seconds. The controller will shut down the device if the sensed current 80 still higher than the predetermined current threshold 81 after the first predetermined period 84.

It is very important to make the gap 82 between two pulses greater than the duration 83 of each pulse. If the gap 82 has equally size to the duration 83, the current 80 of the motor will not go to zero. In other words, making the current speed of the motor going to zero (OFF) in a very short time, and ON again. It will provide the effect of the pulsating bristle tuft motions.

The reason behind it is that the controller will make the rotary motion of the torque assembly in the pulsating bristle tuft motions. The motor does not have enough power to drive all gear teeth of the spiral shaft and the spiral gear of each brush set work properly. A person can be physically noticed through gums and teeth due to the gear motions, and the person can even hear the "tic tac" sound from the brush head.

It is noted that the pulse activated mode of the controller can not be considered as Pulse Width Modulation mode. PWM is a modulation technique that controls the width of the pulse and turning the load on and off at a fast pace. The switching frequency of PWM has to be much higher than what would affect the load. The pulse activated mode works totally in an opposite way, it wants to affect the load so the user is able to physically feel the notification from the teeth and gums. In actual practice, the 7200 rpm of the motor is about 120 Hz, the frequency of the pulse activated mode is about 1.4 Hz (0.7 second per cycle, as shown in FIG. 6a). Accordingly, the switching frequency of the controller in accordance of the present invention is much smaller than the frequency of the load (i.e., the motor).

FIG. 6b shows another embodiment which the sensed current 80 exceeds the predetermined current threshold 81 but not longer than the first predetermined period 84. In this embodiment, the person release the pressure of the brush sets when he/she feels the pulsating bristle tuft motions from the device, and the sensed current 80 then decrease below the predetermined current threshold 81. The controller will then energize the motor back to the DC mode. FIG. 6c shows yet another embodiment which the device has been shut down after the second predetermined period 85, regardless the level of the sensed current 80 but the operational time of the controller.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

What is claimed is:
1. An electric toothbrush, comprising:
a brush head having a plurality of exposed brush sets;
a motor being connected to the brush head, which is configured for driving the exposed brush sets; and
a controller driving the motor with a power module, and sensing a current of the motor which disables the motor after a first predetermined period when the sensed current exceeds a predetermined current threshold, wherein the controller then drives the motor in a Direct Current (DC) mode, and drives the motor in a pulse activated mode when and if the sensed current still exceeds the predetermined current threshold.

2. The toothbrush as claimed in claim 1, further comprising a indicator connected to the controller, and the power module is a battery pack, wherein the indicator is configured for indication when the power volume of the power module is below a volume threshold.

3. The toothbrush as claimed in claim 1, further comprises a timer that counts an operational time of the motor, and instructs the controller to disable the motor when the operational time exceeds a second predetermined period.

4. The toothbrush as claimed in claim 3, further comprises a wired transmitting module or a wireless transmitting module, which is able to allow a person to adjust the second predetermined period from an external user interface.

5. The toothbrush as claimed in claim 1, further comprises a wired transmitting module or a wireless transmitting module, which is able to allow a person to adjust the first predetermined period or the predetermined current threshold from an external user interface.

* * * * *